United States Patent
Salahutdinov et al.

(10) Patent No.: US 8,809,391 B2
(45) Date of Patent: Aug. 19, 2014

(54) AGENT FOR TREATING PARKINSON'S DISEASE

(75) Inventors: Nariman Faridovich Salahutdinov, Novosibirsk (RU); Tatiana Genrihovna Tolstikova, Novosibirsk (RU); Alla Viktorovna Pavlova, Novosibirsk (RU); Ekaterina Aleksandrovna Morozova, Novosibirsk (RU); Irina Viktorovna Il'ina, Novosibirsk (RU); Oleg Vasil'evich Ardashov, Novosibirsk (RU); Konstantin Petrovich Volcho, Novosibirsk (RU)

(73) Assignee: OOO "Tomskaya Farmatsevticheskaya Fabrika", Tomsk (RU)

( * ) Notice: Subject to any disclaimer, the term of this patent is extended or adjusted under 35 U.S.C. 154(b) by 0 days.

(21) Appl. No.: 13/518,814

(22) PCT Filed: Dec. 23, 2010

(86) PCT No.: PCT/RU2010/000778
§ 371 (c)(1), (2), (4) Date: Jun. 22, 2012

(87) PCT Pub. No.: WO2011/093742
PCT Pub. Date: Aug. 4, 2011

(65) Prior Publication Data
US 2013/0116319 A1   May 9, 2013

(30) Foreign Application Priority Data

Dec. 24, 2009 (RU) ................. 2009148376

(51) Int. Cl.
*C07C 35/18* (2006.01)
*C07C 69/96* (2006.01)
*A61K 31/047* (2006.01)
*A61K 31/015* (2006.01)
*A61K 31/215* (2006.01)

(52) U.S. Cl.
CPC .............. *C07C 35/18* (2013.01); *C07C 69/96* (2013.01); *A61K 31/047* (2013.01); *A61K 31/015* (2013.01); *A61K 31/215* (2013.01)
USPC ......................................... 514/512; 514/729

(58) Field of Classification Search
USPC ................................................... 514/512, 729
See application file for complete search history.

(56) References Cited

U.S. PATENT DOCUMENTS 6,379,666 B1 * 4/2002 Tobinick ................... 424/134.1

FOREIGN PATENT DOCUMENTS

RU         2355390 C1     5/2009

OTHER PUBLICATIONS

Vegerovsky, A. I., "Pharmacology lectures for doctors and pharmacists," STT. 1988, pp. 181-186, Tomsk, Russia.
Aminoff M. D., "Pharmacologic Management of Parkinsonism & Other Movement Disorders: Introduction," Basic and Clinical Pharmacology, eighth edition, edited by Katsung B. G., 2007, pp. 539-555, McGraw-Hill Companies.
Il'ina, I. V., et al., "Reactions of Allyl Alcohols of the Pinane Series and of Their Epoxides in the Presence of Montmorillonite Clay," Helvetica Chimica Acta, 2007, pp. 353-368, V. 90.
Ratner, V. V., et al., "Oxidation of Carene by Thallium(III) Acetate," UDC 542.943.7:547.597, Translated from Izvestiya Akademii Nauk SSSR, Seriya Khimicheskaya, Aug. 1983, pp. 1824-1828, No. 8.
Kawasaki T., et al., "A neuroprotective agent, T-817MA (1-{3-[2-(1-benzothiophen-5-yl)ethoxy]propyl} azetidin-3-ol maleate), prevents 1-methyl-4-phenyl-1,2,3,6-tetrahydropyridine induced neurotoxicity in mice," Neuropharmacology, 2008, pp. 654-660, V. 55.
Dingemanse, J., "Catechol-O-methyltransferase Inhibitors: Clinical Potential in the Treatment of Parkinson's Disease," Drug Development Research, 1997, pp. 1-25, V. 42.
Quik, M., et al., "Nicotinic receptors as CNS targets for Parkinson's disease," Biochemical Pharmacology, 2007, pp. 1224-1234, V. 74.
Rukovodstvo po meditsine. Diagnostika i terapia, M., "MIR", 1997, vol. 1, pp. 1018-1023.
International Search Report dated Jul. 25, 2011 from corresponding PCT Application No. PCT/RU2010/2010/000778, filed Dec. 23, 2010.

* cited by examiner

*Primary Examiner* — San-Ming Hui
*Assistant Examiner* — Kathrien Cruz
(74) *Attorney, Agent, or Firm* — Patentbar International, P.C.

(57) ABSTRACT

The present invention relates to the use of 3-methyl-6-(1-methylethenyl)cyclohex-3-ene-1,2-diol, its isomers and derivatives, as a compound for Parkinson disease treatment, that can be used in medicine. The compound is highly active, low toxic and can be synthesized from available natural compound α-pinene. 13 ex., 7 tables.

14 Claims, No Drawings

AGENT FOR TREATING PARKINSON'S DISEASE

RELATED APPLICATIONS

This application is a U.S. National Stage application of PCT application Ser. No. PCT/RU2010/000778 filed on Dec. 23, 2010 which claims priority to Russian Patent Application No. 2009148376, filed Dec. 24, 2009, the contents of which are both incorporated herein by reference in their entirety.

FIELD OF THE INVENTION

The invention relates to the field of medicine, in particular, to new drug that can be used in Parkinson disease treatment.

BACKGROUND OF THE INVENTION

Parkinson disease is one of the most widespread neurological disorders accompanied by movement disorders, caused mainly by the loss of dopamine-containing cells of the nigrastrial pathway. The prevalence of Parkinson disease is 1% of adult population under 60 years of age, 5-10%—in population of 60-80 years of age [1]. Parkinson disease requires prolonged treatment, sometimes during the whole life, and requires combining different drugs, usually dopamine system agonists and anticholinetics.

Different drugs are used in Parkinson disease treatment. The most used are drugs containing L-DOPA—a dopamine precursor (levodopa, carbidopa, nakom). These drugs are used as substitution therapy, because the disease is associated with the reduction of dopamine level. Other drugs are used: drugs suppressing the stimulating action of cortical glutamate receptors, which develops on the background of dopamine level reduction (midantan); dopamine (peripheral) receptors agonists (ropinirole); MAO-B inhibitors (selegiline) and central anticholinetics.

The main drug of antiparkinson therapy, effectively eliminating the disease symptoms, is levodopa. Antiparkinson action of levodopa is caused by its transformation into dopamine in the CNS. However, only 1-3% of the administered drug reach the target (brain) so levodopa is usually combined with peripheral DOPA-carboxylase inhibitors (carbidopa, etc.), raising the percentage of levodopa reaching the brain up to 10% [2].

The drawback of levodopa-containing drugs are [1, 2]: 1) low effectiveness (the drug is highly effective in ⅓ of patients and less effective in another ⅓, the rest of patients are intolerant to the drug or do not experience its positive effects at all); 2) many adverse effects (anorexia, vomiting, tachycardia, dyskinesia, appearing in almost 80% of patient, mental disorders, etc.); 3) movement fluctuations ("on-off" syndrome); 4) drug tolerance—after 3-4 years of levodopa therapy its efficiency often decreases, up to total inefficiency, independent of the patient's condition in the beginning of treatment, so the treatment of moderate parkinsonism is avoided until the disease starts to affect the patient's normal life significantly; however, it is shown [2], that early start of treatment reduces mortality associated with Parkinson disease.

To reduce the required dose and adverse effects levodopa is usually combined with other drugs, but they do not eliminate the aforementioned drawbacks completely [1, 2], and these drugs are insufficiently effective without levodopa.

As for the drugs having potentiating effect on dopaminergic system, the presence of such effect is insufficient to prove that the compound can significantly affect dopaminergic system without L-DOPA and have antiparkinson activity.

Due to these factors, the search and creation of new low-toxic antiparkinson drugs continues to be relevant in the present time.

SUMMARY OF THE INVENTION

We have shown, that a compound of general formula 1, and its spatial isomers, including optically active ones, can be used as an effective low-toxic agent for Parkinson disease treatment.

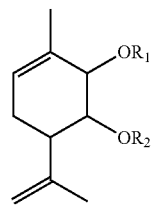

1 in which R1, R2 may be different or the same, and may be hydrogen atoms, C1-C6-carbonic acid residue composing an ether group (unsubstituted or substituted by halogen atoms, the halogen atom may be any of the following: F, CL, I, Br).

The compound 1a (where $R_1=R_2=H$) was synthesized and described in articles [3, 4], data on its antiparkinson activity is absent in the literature.

The compound can be synthesized in accordance with the scheme 1, using a readily available domestic plant material—monoterpene α-pinene and available reagents [3] or by other methods (for example, in accordance with [4]).

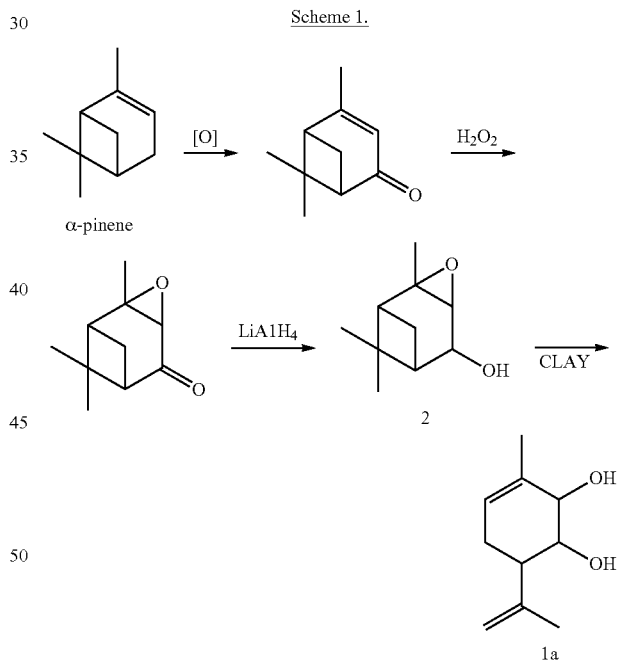

Scheme 1.

To synthesize the compound of the general formula 1 as different isomers (including optically active ones) different spatial isomers of the reactants, including optically active ones, can be used:

Synthesis of compounds of general formula 1, where both/either $R_1$ and/or $R_2 \neq H$ may be done from compound 1a or by other methods.

To study antiparkinson activity in vivo 1-methyl-4-phenyl-1,2,3,6-tetrahydropyridine (MPTP) is widely used, causing Parkinson disease in humans, monkeys, rats, mice [2,5-7].

Parkinsonism was induced by single and multiple intraperitoneal administration of MPTP in 30 mg/kg doses in male mice of C57B1/6 strain and Wistar rats.

Antiparkinson activity of the compound of general formula 1 was studied in vivo in MPTP-induced parkinsonism model. Levodopa (L-DOPA) was used as the drug of comparison.

Antiparkinson activity of the agents was studied by the degree of hypokinesia and locomotor activity using Truscan apparatus (USA) or by mortality percentage.

The compound (1R,2R,6S)-1a with an enantiomeric excess (ee) of 60%, corresponding to enantiomeric excess present in commercially available verbenone and domestic plant-derivedα-pinene, administered in doses of 10, 20 and 30 mg/kg was shown to have a potent antiparkinson activity in MPTP-induced (single and multiple administration) parkinsonism in mice. The activity manifested in the animals' locomotor activity increase (general movement, movement distance, speed and duration) and emotional condition improvement (number of explored holes). 20 mg/kg dose was observed to be the most effective.

Agent (1R,2R,6S)-1a with an ee of 60% in a 20 mg/kg dose exhibits remarkable antiparkinson activity in rats during a 30-day administration of the agent and MPTP as evidenced by locomotor activity increase (general movement, movement distance, speed, duration) and emotional condition improvement (number of explored holes and rearings).

Agent (1R,2R,6S)-1a with an ee of 60% in a 20 mg/kg dose was as effective as the reference drug levodopa in these tests.

The stereochemical structure of the compound of the general formula 1 was shown to have a considerable impact on its antiparkinson activity. For example, although agents (1R,2R,6S)-1a with an ee of 94% and (1S,2S,6R)-1a with an ee of 97% exhibit pronounced antiparkinson activity following a single administration of MPTP, agent (1R,2R,6S)-1a with an ee of 60% was shown to be the most effective.

The compounds of the general formula 1, where R1 and/or R2≠H were also shown to have antiparkinson activity. For example, agent (1R,2R,6S)-1b (R1=R2=Ac) with an ee of 60% in a 20 mg/kg dose exibits considerable antiparkinson activity following a single and multiple administration of MPTP, manifesting in the improvement of the animals' locomotor activity and emotional condition improvement.

The acute toxicity of the compound 1a was studied in white outbred mice weighting 20-22 g following single intragastric administration using Kerber method. The compound 1a was shown to have low toxicity, LD50 is 4250 mg/kg.

It can thus be said, that the compound of general formula 1 combines low toxicity and potent antiparkinson activity, is as effective as the drug of comparison levodopa, and can be used, after the required trials, as a stand-alone drug or as a component of highly effective dosage forms for treating Parkinson disease. The required single dose will depend on the patient's gender, age, weight, severity of the disease, and will preferably be from 1 to 500 mg.

EXAMPLES

The invention is described by the following examples.

Example 1

Synthesis of 3-methyl-6-(1-methylethenyl)cyclohex-3-ene-1,2-diol1a using askanite-bentonite clay

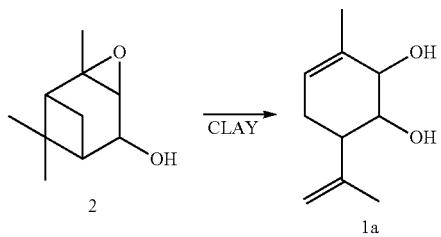

A solution of 0.2 g of verbenole epoxide 2 in 7 ml $CH_2Cl_2$ was added into a suspension of 0.5 askanite-betonite clay (calcinated for 3 hours under 120° C.) in 8 ml $CH_2Cl_2$. The mixture was mixed for 40 minutes under 20° C. 5 ml of diethylether was then added. The catalyst was filtered, the solvent evaporated. The obtained reaction mixture was separated in a column with 10 g of silicate gel, a solution of diethyl ether in hexane 10 to 90% was used as an eluent. 0.094 g (47%) of 3-methyl-6-(1-methylethenyl)cyclohex-3-ene-1,2-diol 1a was obtained as a result.

Example 2

Synthesis of (1R,2R,6S)-3-methyl-6-(1-methylethenyl)cyclohex-3-ene-1,2-diol ((1R,2R,6S)-1a) with ee 60% using K10 clay

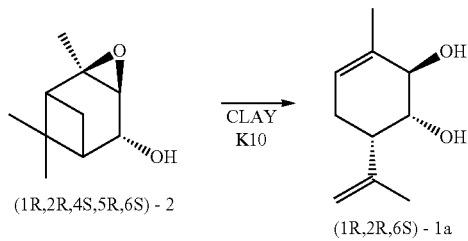

A solution of 11.5 g of epoxide (−)-cis-verbenole (1R,2R,4S,5R,6S)-2 ([α]$_{580}^{20}$=−44 (c 12, $CHCl_3$)) in 150 ml $CH_2Cl_2$ was added, stiffing continuously, into a suspension of 30 g K10 (Fluka) clay (calcinated for 3 hours under 110° C.) in 200 ml $CH_2Cl_2$. The reaction mixture was stirred for 1 hour under 22° C. The catalyst was filtered, rinsed by ethyl acetate, the solvent was evaporated. The residue was separated by column chromatography using silicate gel, a solution of ethyl acetate in hexane 5 to 100% was used as an eluent. 5.10 g (44%) of (1R,2R,6S)-3-methyl-6-(1-methylethenyl)cyclohex-3-ene-1,2-diol ((1R,2R,6S)-1a) (ee 60%, [α]$_{580}^{20}$=−46(c 18, $CHCl_3$)) was obtained as a result. Enantiomeric purity of the compound 1a was evaluated by the data of gas-liquid chromatography with mass spectroscopy in chiral column.

Example 3

Synthesis of (1R,2R,6S)-3-methyl-6-(1-methylethenyl)cyclohex-3-ene-1,2-diol ((1R,2R,6S)-1a) with ee 94% using K10 clay

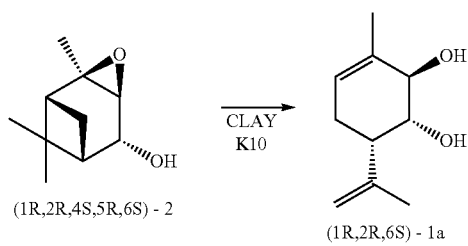

A solution of 945 mg epoxide (−)-cis-verbenole (1R,2R,4S,5R,6S)-2 ([α]$_D^{25}$=−85.6 (c0.82, $CHCl_3$)) in 12 ml methylene chloride was added, stiffing continuously, into a suspension of 2 g K10 (Fluka) clay (calcinated for 3 hours under 110° C.) in 15 ml of methylene chloride. The reaction mixture was stirred for 1 hour under room temperature. The catalyst was filtered, rinsed by ethyl acetate, the solvent was evaporated. The residue was separated by column chromatography using SiO$_2$ (60-200µ; Merck), a solution of diethyl ether in hexane 5 to 100% was used as an eluent. 270 mg (29%) of (1R,2R,6s)-1a (ee 94%, ($[\alpha]_D^{27}$=−84.0 (c 3.47, CHCl$_3$)) was obtained as a result. Enantiomeric purity of the compound 1a was evaluated by the data of gas-liquid chromatography with mass spectroscopy in chiral column.

Example 4

Synthesis of (1S,2S,6R)-3-methyl-6-(1-methylethenyl)cyclohex-3-ene-1,2-diol ((1S,2S,6R)-1a) with ee 94% using K10 clay

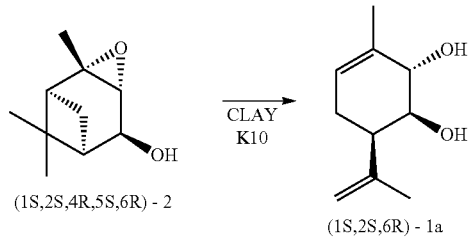

A solution of 850 mg (5.05 mmol) epoxide (+)-cis-verbenole (1S,2S,4R,5S,6R)-2 in 12 ml methylene chloride was added, stiffing continuously, into a suspension of 2 g K10 (Fluka) clay (calcinated for 3 hours under 110° C.) in 15 ml of methylene chloride. The reaction mixture was stirred for 1 hour under room temperature. The catalyst was filtered, rinsed by ethyl acetate, the solvent was evaporated. The residue was separated by column chromatography using SiO$_2$ (60-200µ; Merck), a solution of diethyl ether in hexane 5 to 100% was used as an eluent. 333 mg (39%) of (1S,2S,6R)-3-methyl-6-(1-methylethenyl)cyclohex-3-ene-1,2-diol ((1S,2S,6R)-1a) (ee 97%, $[\alpha]_D^{23}$+82.7 (c 0.726, CHCl$_3$)) was obtained as a result. Enantiomeric purity of the compound 1a was evaluated by the data of gas-liquid chromatography with mass spectroscopy in chiral column.

Example 5

Synthesis of (1S,2R,6S)-3-methyl-6-(1-methylethenyl)cyclohex-3-ene-1,2-diol((1S,2R,6R)-1a) with ee 94% using K10 clay

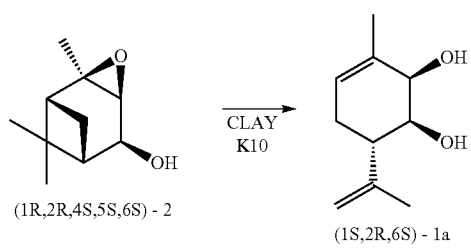

A solution of 425 mg epoxide (−)-trans-verbenole (1R,2R,4S,5S,6S)-2 ($[\alpha]_D^{29}$=−118.6 (c 4.44, CHCl$_3$)) in 7 ml methylene chloride was added, stiffing continuously, into a suspension of 1 g K10 clay (calcinated for 3 hours under 110° C.) in 8 ml methylene chloride. The reaction mixture was stirred for 1 hour under room temperature. The catalyst was filtered, rinsed by ethyl acetate, the solvent was evaporated. The residue was separated by column chromatography using SiO$_2$ (60-200µ; Merck), a solution of diethyl ether in hexane 5 to 100% was used as an eluent. 75 mg (11%) of (1S,2R,6S)-3-methyl-6-(1-methylethenyl)cyclohex-3-ene-1,2-diol((1S, 2R,6R)-1a) (ee94%, $[\alpha]_D^{29}$=−90.1 (c 6.10, CHCl$_3$)) was obtained as a result. Enantiomeric purity of the compound 1a was evaluated by the data of gas-liquid chromatography with mass spectroscopy in chiral column.

Example 6

Synthesis of diacetate (1R,2R,6S)-3-methyl-6-(1-methylethenyl)cyclohex-3-ene-1,2-diol(1R,2R,6S)-1b

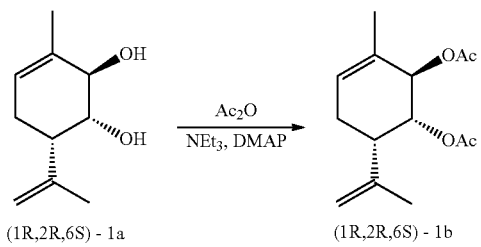

6 ml of ether, 1 ml of triethylamine and one crystal of N,N-4-dimethylaminopyridine (DMAP) were added to 168 mg of the compound (1R,2R,6S)-1a. After 4 hours the compound was rinsed by 2×10 ml 3.5% HCl, 2×10 ml 5% NaHCO$_3$ and 10 ml of water, dried using MgSO$_4$, the solvent was evaporated. 252 mg (100%) diacetate (1R,2R,6S)-3-methyl-6-(1-methylethenyl)cyclohex-3-ene-1,2-diol (1R,2R,6S)-1b was obtained as a result. $[\alpha]_D^{27}$=−77.0 (c 6.87, CHCl$_3$). $^1$H-NMRspectrum (CDCl$_3$), δ$_H$, ppm (J, Hz): 1.64 d. d. d. (C$^{10}$H$_3$, J$_{10,5a'}$ 2.2 Hz, J$_{10,4}$ 1.5 Hz, J$_{10,5e'}$ 1.5 Hz), 1.74 br. s. (C$^9$H$_3$), 1.96 s. and 2.07 s. (C$^{12}$H$_3$, C$^{14}$H$_3$), 2.03 d. d. d. q. (H$^{5e'}$, J$_{5e',5a'}$ 16.5 Hz, J$_{5e',4}$ 5.0 Hz, J$_{5e',6a}$ 4.5 Hz, J$_{5e',10}$ 1.5 Hz), 2.28 d. d. d. q. d. (H$^{5a'}$, J$_{5a',5e'}$ 16.5 Hz, J$_{5a',6a}$ 11.0 Hz, J$_{5a',4}$ 2.2 Hz, J$_{5a',10}$ 2.2 Hz, J$_{5a',2e'}$ 1.2 Hz), 2.38 br. d. d. (H$^{6a}$, J$_{6a,5a'}$ 11.0 Hz, J$_{6a,5e'}$ 4.5 Hz), 4.69 br. s. and 4.81 m. (2 H$^8$), 5.10 br. d. (H$^{2e'}$, J$_{2e',1e'}$ 3.0 Hz), 5.15 d. d. (H$^{1e}$, J$_{1e,2e'}$ 3.0 Hz, J$_{1e,6a}$ 1.5 Hz), 5.76 d. d. q. (H$^4$, J$_{4,5e'}$ 5.0 Hz, J$_{4,5a'}$ 2.2 Hz, J$_{4,10}$ 1.5 Hz).

Example 7

Study of Antiparkinson Activity of (1R,2R,6S)-3-methyl-6-(1-methylethenyl)cyclohex-3-ene-1,2-diol ((1R,2R,6S)-1a) with ee 60% in Mice After Single Administration of Neurotoxin Experiments were carried out in male mice of C57B1/6 strain in groups of 10 mice each. Parkinson syndrome was induced by intraperitoneal administration of 30 mg/kg dose of MPTP, saline was administered to intact control group. The agent was administered per os 15 minutes after the reproduction of Parkinson syndrome. Hypokinesia was evaluated 1.5 hours after MPTP injection by the degree of locomotor activity using TruScan apparatus (USA) during 3 minutes.

The results of experiments are shown in Table 1.

TABLE 1

Study of antiparkinson activity of the compound (1R,2R,6S)-1a with ee 60% in mice following single administration of MPTP.

| Group, dose | A | B | C | D | E | F | G |
|---|---|---|---|---|---|---|---|
| Control I, saline | 82 ± 1.97** | 66.6 ± 2.31*** | 309.3 ± 17.94*** | 2.54 ± 0.14*** | 4.7 ± 0.96 | 2.1 ± 0.56 | 11.6 ± 1.4** |
| Control II, MPTP 30 mg/kg | 59 ± 3.8 | 39.8 ± 5.8 | 171.4 ± 37 | 1.3 ± 0.3 | 4.9 ± 0.9 | 2.5 ± 0.5 | 5 ± 1.6 |
| MPTP 30 mg/kg and (1R,2R,6S)-1a, 10 mg/kg | 77.2 ± 5** | 57 ± 5.3* | 257.3 ± 29.5 | 2.1 ± 0.25 | 7.7 ± 1.07 | 3.6 ± 0.7 | 5.8 ± 0.6 |
| MPTP 30 mg/kg and (1R,2R,6S)-1a, 20 mg/kg | 80.7 ± 4** | 59 ± 4** | 276.5 ± 24* | 2.25 ± 0.2* | 7.6 ± 1.7 | 4.4 ± 1 | 8.5 ± 2 |

*$P < 0.05$;
**$P < 0.01$;
***$P < 0.001$ stat. significance compared to control group II
A - general movement activity (number of movement acts);
B - movement activity (seconds);
C - movement distance (cm);
D - movement speed (cm/sec);
E - number of explored holes;
F - time of exploratory activity (sec);
G - number of rearings.

Experiment has shown that agent (1R,2R,6S)-1a with ee 60% in 10 and 20 mg/kg doses exhibits remarkable antiparkinson activity after single administration of MPTP as evidenced by locomotor activity increase (general movement, movement distance, speed, duration) and emotional condition improvement (number of explored holes and rearings). The best effect was achieved in 20 mg/kg dose.

Example 8

Study of Antiparkinson Activity of (1R,2R,6S)-3-methyl-6-(1-methylethenyl)cyclohex-3-ene-1,2-diol ((1R,2R,6S)-1a) with ee 60% in Mice After 3 Days of Neurotoxin Administration Experiments were carried out in male mice of C57B1/6 strain in groups of 10 mice each. Parkinson syndrome was induced by intraperitoneal administration of 30 mg/kg dose of MPTP during 3 days. The agent ((1R,2R,6S)-1a was administered per os in 20 mg/kg and 30 mg/kg doses 24 hours after the last MPTP injection. Hypokinesia was evaluated 1 hour after the agent administration by the degree of locomotor activity using TruScan apparatus (USA) during 3 minutes.

The results of experiments are shown in Table 2.

TABLE 2

Study of antiparkinson activity of the compound (1R,2R,6S)-1a with ee 60% in mice following 3 days administration of MPTP.

| Group, dose | A | B | C | D | E | F | G |
|---|---|---|---|---|---|---|---|
| Control, MPTP 30 mg/kg | 43.4 ± 4.7 | 55.5 ± 6.0 | 264.5 ± 34.8 | 2.2 ± 0.3 | 1.8 ± 0.6 | 1 ± 0.3 | 12.2 ± 2.0 |
| MPTP 30 mg/kg and (1R,2R,6S)-1a, 20 mg/kg | 81.9 ± 3.7** | 70.1 ± 3.9* | 351.8 ± 26.4* | 2.9 ± 0.2 | 8.8 ± 1.0*** | 3.9 ± 0.5*** | 11.1 ± 0.9 |

TABLE 2-continued

Study of antiparkinson activity of the compound (1R,2R,6S)-1a with ee
60% in mice following 3 days administration of MPTP.

| Group, dose | A | B | C | D | E | F | G |
|---|---|---|---|---|---|---|---|
| MPTP 30 mg/kg and (1R,2R,6S)-1a, 30 mg/kg | 81.8 ± 2.6** | 66.8 ± 3.7 | 335.5 ± 28.9 | 2.7 ± 0.2 | 3.8 ± 0.6* | 1.6 ± 0.3 | 13 ± 1.7 |

*$P < 0.05$;
**$P < 0.01$;
***$P < 0.001$ stat. significance compared to control group
A - general movement activity (number of movement acts);
B - movement activity (seconds);
C - movement distance (cm);
D - movement speed (cm/sec);
E - number of explored holes;
F - time of exploratory activity (sec);
G - number of rearings.

Experiment has shown that agent (1R,2R,6S)-1a with ee 60% in 20 mg/kg and 30 mg/kg doses exhibits remarkable antiparkinson activity after single administration of MPTP as evidenced by locomotor activity increase (general movement, movement distance, speed, duration) and emotional condition improvement (number of explored holes and rearings). The best effect was achieved in 20 mg/kg dose.

Example 9

Study of Antiparkinson Activity of the Compound (1R,2R,6S)-1a with ee 60% in Mice in 10 Days Administration of MPTP and the Agent Experiments were carried out in male mice of C57Bl/6 strain in groups of 10 mice each. Parkinson syndrome was induced by intraperitoneal administration of 30 mg/kg dose of MPTP daily during 10 days. The agent ((1R,2R,6S)-1a in 20 mg/kg dose and levodopa (the drug of comparison) in 10 mg/kg dose were administered per os 4 hours after MPTP injection daily during 10 days. The effect was evaluated by the number of surviving animals on the 11 day of the experiment.

The results of experiments are shown in Table 3.

TABLE 3

Study of antiparkinson activity of the compound (1R,2R,6S)-1a with
ee 60% in mice in 10 days administration of MPTP and the agent.

| | Control, MPTP 30 mg/kg | MPTP 30 mg/kg and (1R,2R,6S)-1a, 20 mg/kg | MPTP 30 mg/kg and L-DOPA, 10 mg/kg |
|---|---|---|---|
| Mortality, % | 60 | 10 | 20 |

The experiment has shown that the agent (1R,2R,6S)-1a with ee 60% in 20 mg/kg dose during 10 days of administration of the agents and MPTP considerably reduces mortality, thus possessing remarkable antiparkinson activity. The agent (1R,2R,6S)-1a with ee 60% is as good as the drug of comparison levodopa in this test.

Example 10

Study of Antiparkinson Activity of the Compound (1R,2R,6S)-1a with ee 60% in Rats in 30 Days Administration of MPTP and the Agent Experiments were carried out in male Wistar rats in groups of 10 mice each. Parkinson syndrome was induced by intraperitoneal administration of 40 mg/kg dose of MPTP daily during 30 days. Saline was administered to intact control group. The agent ((1R,2R,6S)-1a in 20 mg/kg dose and levodopa (the drug of comparison) in 10 mg/kg dose were administered per os 4 hours after MPTP injection daily during 30 days. Hypokinesia was evaluated on 30 day of experiment by the degree of locomotor activity using TruScan apparatus (USA) during 3 minutes.

The results of experiments are shown in Table 4.

TABLE 4

Study of antiparkinson activity of the compound (1R,2R,6S)-1a with ee
60% in rats in 30 days administration of MPTP and the agent.

| Group, dose | A | B | C | D | E | F | G |
|---|---|---|---|---|---|---|---|
| Control, I, saline | 80.3 ± 2.5** | 69.68 ± 2.11*** | 367.5 ± 21.2*** | 3.02 ± 0.17*** | 4.6 ± 0.87 | 1.85 ± 0.24 | 14.6 ± 1.82*** |
| Control II, MPTP 30 mg/kg | 50.36 ± 7.9 | 27.77 ± 4.78 | 110.4 ± 19.5 | 0.87 ± 0.15 | 2.7 ± 0.99 | 1.57 ± 0.68 | 2.55 ± 0.76 |

TABLE 4-continued

Study of antiparkinson activity of the compound (1R,2R,6S)-1a with ee 60% in rats in 30 days administration of MPTP and the agent.

| Group, dose | A | B | C | D | E | F | G |
|---|---|---|---|---|---|---|---|
| MPTP 30 mg/kg and (1R,2R,6S)-1a, 20 mg/kg | 81.89 ± 5.5** | 62.56 ± 5.2*** | 305.58 ± 30.38*** | 2.5 ± 0.25*** | 4.3 ± 0.73 | 1.75 ± 0.5 | 10.67 ± 1.18*** |
| MPTP 30 mg/kg and L-DOPA, 10 mg/kg | 86 ± 3.86** | 65.09 ± 2.92*** | 316.77 ± 16.2*** | 2.57 ± 0.13*** | 4.63 ± 0.56 | 1.66 ± 0.25 | 9.63 ± 1.16*** |

*$P < 0.05$;
**$P < 0.01$;
***$P < 0.001$ stat. significance compared to control group II.
A - general movement activity (number of movement acts);
B - movement activity (seconds);
C - movement distance (cm);
D - movement speed (cm/sec);
E - number of explored holes;
F - time of exploratory activity (sec);
G - number of rearings.

Experiment has shown that agent (1R,2R,6S)-1a with ee 60% in 20 mg/kg dose exhibits remarkable antiparkinson activity after 30 days administration of MPTP and the agent, as evidenced by locomotor activity increase (general movement, movement distance, speed, duration) and emotional condition improvement (number of explored holes and rearings). The agent (1R,2R,6S)-1a with ee 60% is as good as the drug of comparison levodopa in this test.

Example 11

Study of Antiparkinson Activity of Compounds (1R,2R,6S)-1a with ee 94% and (1S,2S,6R)-1a with ee 97% in Mice after Single Administration of Neurotoxin Experiments were carried out in male mice of C57B1/6 strain in groups of 10 mice each. Parkinson syndrome was induced by intraperitoneal administration of 30 mg/kg dose of MPTP, saline was administered to intact control group. The agents in 20 mg/kg doses were administered per os 15 minutes after the reproduction of Parkinson syndrome. Hypokinesia was evaluated 1.5 hours after MPTP injection by the degree of locomotor activity using TruScan apparatus (USA) during 3 minutes.

The results of experiments are shown in Table 5.

TABLE 5

Study of antiparkinson activity of compounds (1R,2R,6S)-1a with ee 94% and (1S,2S,6R)-1a with ee 97% in mice after single administration of MPTP.

| Group, dose | A | B | C | D | E | F | G |
|---|---|---|---|---|---|---|---|
| Control, MPTP 30 mg/kg | 50.6 ± 8.1 | 27.8 ± 4.8 | 107.8 ± 20.6 | 0.87 ± 0.15 | 2.8 ± 1.0 | 1.6 ± 0.7 | 2.6 ± 0.8 |
| MPTP 30 mg/kg and (1R,2R,6S)-1a, 20 mg/kg | 78.6 ± 5.0** | 64.0 ± 5.5*** | 332.6 ± 39.6*** | 2.7 ± 0.3*** | 3.2 ± 0.9 | 1.5 ± 0.4 | 13.1 ± 2.5*** |

TABLE 5-continued

Study of antiparkinson activity of compounds (1R,2R,6S)-1a with ee
94% and (1S,2S,6R)-1a with ee 97% in mice after single administration of MPTP.

| Group, dose | A | B | C | D | E | F | G |
|---|---|---|---|---|---|---|---|
| MPTP 30 mg/kg and (1S,2S,6R)-1a, 20 mg/kg | 57.9 ± 6.0 | 34.9 ± 4.3 | 147.8 ± 20.3 | 1.13 ± 0.15 | 2.5 ± 0.9 | 1.2 ± 0.6 | 4.4 ± 1.4 |

*P < 0.05;
**P < 0.01;
***P < 0.001 stat. significance compared to control group
A - general movement activity (number of movement acts);
B - movement activity (seconds);
C - movement distance (cm);
D - movement speed (cm/sec);
E - number of explored holes;
F - time of exploratory activity (sec);
G - number of rearings.

Experiment has shown that agents (1R,2R,6S)-1a with ee 94% and (1S,2S,6R)-1a with ee 97% in 20 mg/kg doses exhibit remarkable antiparkinson activity after single administration of MPTP, as evidenced by locomotor activity increase (general movement, movement distance, speed, duration) and emotional condition improvement (number of explored holes and rearings). Agent (1R,2R,6S)-1a was the most effective one.

Example 12

Study of Antiparkinson Activity of Diacetate (1R,2R,6S)-3-methyl-6-(1-methylethenyl)cyclohex-3-ene-1,2-diol (1R,2R,6S)-1b with ee 60% in Mice after Single Administration of Neurotoxin Experiments were carried out in male mice of C57B1/6 strain in groups of 10 mice each. Parkinson syndrome was induced by intraperitoneal administration of 30 mg/kg dose of MPTP, saline was administered to intact control group. The agent in 10 mg/kg and 20 mg/kg doses were administered per os 15 minutes after the reproduction of Parkinson syndrome. Hypokinesia was evaluated 1.5 hours after MPTP injection by the degree of locomotor activity using TruScan apparatus (USA) during 3 minutes.

The results of experiments are shown in Table 6.

TABLE 6

Study of antiparkinson activity of the compound (1R,2R,6S)-1b with ee
60% in mice after single MPTP administration.

| Group, dose | A | B | C | D | E | F | G |
|---|---|---|---|---|---|---|---|
| Control, MPTP 30 mg/kg | 59 ± 3.8 | 39.8 ± 5.8 | 171.4 ± 37 | 1.3 ± 0.3 | 4.9 ± 0.9 | 2.5 ± 0.5 | 5 ± 1.6 |
| MPTP 30 mg/kg and (1R,2R,6S)-1b, 10 mg/kg | 69.9 ± 6.7 | 51.5 ± 7.5 | 244.4 ± 4.5 | 2.0 ± 0.4 | 3.4 ± 1.1 | 1.3 ± 0.5 | 6.4 ± 1.6 |

TABLE 6-continued

Study of antiparkinson activity of the compound (1R,2R,6S)-1b with ee 60% in mice after single MPTP administration.

| Group, dose | A | B | C | D | E | F | G |
|---|---|---|---|---|---|---|---|
| MPTP 30 mg/kg and (1R,2R,6S)-1b, 20 mg/kg | 84.8 ± 4.4** | 58.8 ± 4.5* | 264.9.5 ± 34.6 | 1.9 ± 0.4 | 3.2 ± 0.5 | 2.0 ± 0.3 | 10.8 ± 1.7** |

*$P < 0.05$;
**$P < 0.01$;
***$P < 0.001$ stat. significance compared to control group
A - general movement activity (number of movement acts);
B - movement activity (seconds);
C - movement distance (cm);
D - movement speed (cm/sec);
E - number of explored holes;
F - time of exploratory activity (sec);
G - number of rearings.

Experiment has shown that agent (1R,2R,6S)-1b with ee 60% in 10 mg/kg and 20 mg/kg doses exhibits remarkable antiparkinson activity after single administration of MPTP as evidenced by locomotor activity increase (general movement, movement distance, speed, duration) and emotional condition improvement (number of explored holes and rearings). The best effect was achieved n 20 mg/kg dose.

Example 13

Study of Antiparkinson Activity of Diacetate (1R,2R,6S)-3-methyl-6-(1-methylethenyl)cyclohex-3-ene-1,2-diol (1R,2R,6S)-1b with ee 60% in mice after 3 Days Administration of Neurotoxin Experiments were carried out in male mice of C57B1/6 strain in groups of 10 mice each. Parkinson syndrome was induced by intraperitoneal administration of 30 mg/kg dose of MPTP daily during 3 days. Agent (1R,2R,6S)-1b with ee 60% in 20 mg/kg dose was administered per os 24 hours after the last MPTP injection. Hypokinesia was evaluated 1.5 hours after MPTP injection by the degree of locomotor activity using TruScan apparatus (USA) during 3 minutes.

The results of experiments are shown in Table 7.

Experiment has shown that agent (1R,2R,6S)-1b with ee 60% in 20 mg/kg dose exhibits remarkable antiparkinson activity after 3 days administration of MPTP as evidenced by locomotor activity increase (general movement, movement distance, speed, duration) and emotional condition improvement (number of explored holes and rearings).

SOURCES OF INFORMATION

1. Vengerovsky A. I. Pharmacology lectures for doctors and pharmacists. Tomsk: STT. 198. P. 181-186.
2. Aminoff M. D. Pharmacotherapy of parkinsonism and other movement disorders. In the book: Basic and clinical pharmacology. V.1. Under edition of Katsung B. G. Moscow: Binom. 2007. P. 539-555.
3. Il'ina I. V., Volcho K. P., Korchagina D. V., Barkhash V. A., Salakhutdinov N. F. Hely. Chim Acta, 2007, V. 90, No 2, P. 353-368.
4. Ratner V. V., Isaeva Z. G., Povodireva I. P., Goryachkina N. F., Efremov Y. A., Arbuzov B. A. Oxidation of 2-carene by thallium acetate (III). USSR Academy of Science News. Chemistry. 1983. No 8. P. 1824-1828.
5. Kawasaki T., Ago Y., Kitao T., Nashida T., Takagi A., Takuma K., Matsuda T. A neuroprotective agent, T-817MA (1-{3-[2-(1-benzothiophen-5-yl)ethoxy]

TABLE 7

Study of antiparkinson activity of the compound (1R,2R,6S)-1b with ee 60% in mice after 3 days of MPTP administration.

| Group, dose | A | B | C | D | E | F | G |
|---|---|---|---|---|---|---|---|
| Control, MPTP 30 mg/kg | 43.4 ± 4.7 | 55.5 ± 6 | 264.5 ± 34.8 | 2.2 ± 0.3 | 1.8 ± 0.6 | 1 ± 0.3 | 12.2 ± 2 |
| MPTP 30 mg/kg and (1R,2R,6S)-1b, 20 mg/kg | 83.9 ± 3.5** | 64.1 ± 5.0 | 310.0 ± 35.6* | 2.5 ± 0.3 | 6.0 ± 1.0** | 3.2 ± 0.8* | 10.4 ± 1.5 |

*$P < 0.05$;
**$P < 0.01$;
***$P < 0.001$ stat. significance compared to control group
A - general movement activity (number of movement acts);
B - movement activity (seconds);
C - movement distance (cm);
D - movement speed (cm/sec);
E - number of explored holes;
F - time of exploratory activity (sec);
G - number of rearings.

propyl}azetidin-3-ol maleate), prevents 1-methyl-4-phenyl-1,2,3,6-tetrahydropyridine-induced neurotoxicity in mice. Neuropharmacology. 2008. V. 55. P. 654-660.
6. Dingemanse J. Catechol-O-methyltransferase Inhibitors: Clinical Potential in the Treatment of Parkinson's Disease. Drug Development Research. 1997. V. 42. P. 1-25.
7. Quik M., Bordia T., O'Leary K. Nicotinic receptors as CNS targets for Parkinson's disease. Biochemical Pharmacology. 2007. V. 74. P. 1224-1234.

What is claimed is:

1. A method of using a medicinal preparation comprising a compound of general formula isomers, including

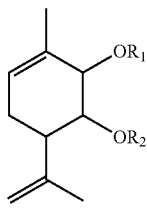

to treat a patient with a Parkinson's disease and/or parkinsonism by administering to the patient a daily dose of the compound ranging from about 1 mg to about 500 mg, wherein R1 and R2 are selected from the group consisting of a hydrogen atom, and a C1-C6-carbonic acid residue composing an ether group.

2. The method of claim 1, wherein the compound of general formula

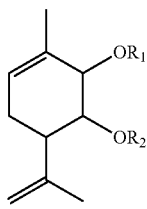

is optically active.

3. The method of claim 1, wherein the compound of general formula

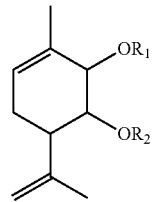

is a spatial isomer.

4. The method of claim 1, wherein R1 and R2 are the same.

5. The method of claim 1, wherein the C1-C6 carbonic acid residue is substituted by a halogen atom selected from the group comprising F, Cl, I, and Br.

6. The method of claim 1, wherein the medicinal preparation is suitable for peroral, sublingual, parenteral or local administration.

7. The method of claim 2, wherein R1 and R2 are the same.

8. The method of claim 2, wherein the C1-C6 carbonic acid residue is substituted by a halogen atom selected from the group comprising F, Cl, I, and Br.

9. The method of claim 2, wherein the medicinal preparation is suitable for peroral, sublingual, parenteral or local administration.

10. The method of claim 3, wherein R1 and R2 are the same.

11. The method of claim 3, wherein the C1-C6 carbonic acid residue is substituted by a halogen atom selected from the group comprising F, Cl, I, and Br.

12. The method of claim 3, wherein the medicinal preparation is suitable for peroral, sublingual, parenteral or local administration.

13. The method of claim 1, wherein administering to the patient a daily dose of the compound ranging from about 1 mg to about 500 mg comprises administering the daily dose of the compound as a stand-alone drug therapy or as a component of a form of treatment.

14. The method of claim 1, wherein administering to the patient a daily dose of the compound ranging from about 1 mg to about 500 mg comprises administering the daily dose of the compound as a stand-alone drug therapy or as a component of a form of treatment.

* * * * *